United States Patent [19]

Kim et al.

[11] Patent Number: 5,991,662
[45] Date of Patent: Nov. 23, 1999

[54] METHOD AND SYSTEM FOR DETECTING DISLODGMENT OF AN IMPLANTED RIGHT ATRIAL ENDOCARDIAL LEAD USING SENSING PERIODS ESTABLISHED WITH ONE OTHER LEAD

[75] Inventors: Jaeho Kim, Redmond; Phillip D. Foshee, Jr., Woodinville, both of Wash.

[73] Assignee: Cardiac Pacemakers, Inc., St. Paul, Minn.

[21] Appl. No.: 09/102,855

[22] Filed: Jun. 23, 1998

[51] Int. Cl.[6] .................................................. A61N 1/37
[52] U.S. Cl. ............................................................ 607/27
[58] Field of Search ........................................ 607/27, 28

[56] References Cited

U.S. PATENT DOCUMENTS 3,768,487  10/1973  Rose .......................................... 607/27
5,003,975  4/1991  Hafelfinger et al. ....................... 607/28
5,476,485  12/1995  Ginberg et al. ............................ 607/28

*Primary Examiner*—William E. Kamm
*Attorney, Agent, or Firm*—Foley & Lardner

[57] ABSTRACT

A system and method are provided for detecting dislodgment of a right atrial endocardial lead implanted within a heart right atrium wherein the lead includes an electrode. Atrial and ventricular activity of the heart are sensed with one other lead during a time period. Also during the time period, heart activity is sensed with the endocardial lead electrode. The sensed heart activity is stored in memory. The stored heart activity sensed with the one other lead is analyzed to establish a first time window from the sensed atrial heart activity and a second time window from the sensed ventricular activity. The heart activity sensed with the endocardial lead electrode during the first time window is then compared to the heart activity sensed with the endocardial lead electrode during the second time window.

13 Claims, 2 Drawing Sheets

METHOD AND SYSTEM FOR DETECTING DISLODGMENT OF AN IMPLANTED RIGHT ATRIAL ENDOCARDIAL LEAD USING SENSING PERIODS ESTABLISHED WITH ONE OTHER LEAD

BACKGROUND OF THE INVENTION

The present invention generally relates to a method and system for detecting dislodgment of an implanted right atrial endocardial lead. The present invention is more particularly directed to such a system and method incorporated within an implantable atrial defibrillator having, in addition to atrial fibrillation cardioversion capability, at least atrial pacing, and more particularly, atrial antitachycardia pacing capability.

Atrial fibrillation is probably the most common cardiac arrhythmia. Although it is not usually a life-threatening arrhythmia, it is associated with strokes thought to be caused by blood clots forming in areas of stagnant blood flow as a result of prolonged atrial fibrillation. In addition, patients afflicted with atrial fibrillation generally experience rapid and irregular beating of the heart and may even experience dizziness as a result of reduced cardiac output.

Atrial fibrillation occurs suddenly, and many times can only be corrected by discharging electrical energy into the atria of the heart of the patient. This treatment is preferably synchronized to a detected R wave of the heart in order to avoid shocking the atria during the T wave or vulnerable period of the heart. The amount of energy which may be required to successfully cardiovert the atria can be as low as one joule and as high as six joules. In most cases, energy of about two to four joules is required to cardiovert atrial fibrillation back to normal sinus rhythm (NSR).

Atrial tachycardia is a less common accelerated atrial arrhythmia. It is a more organized arrhythmia than atrial fibrillation characterized by a very fast and substantially constant atrial rate. Atrial tachycardia results in many of the same symptoms as atrial fibrillation. It can result in dizziness, shortness of breath and a rapid ventricular rate.

Implantable atrial defibrillators are known which detect the presence of atrial fibrillation and provide a single cardioverting pulse of electrical energy to the atria when atrial fibrillation is detected. Usually, the therapy is applied in synchrony with a detected R wave to avoid therapy application during the ventricular vulnerable period of the heart thereby preventing the induction of a lethal ventricular arrhythmia.

Antitachycardia atrial pacing is often used as a therapy for atrial tachycardia. In such therapy, the atria are paced at a rate faster than the atrial intrinsic rate for a time to terminate the atrial tachycardia. This is commonly known as overdrive pacing.

To accomplish overdrive pacing, the right atrium is commonly paced at a high rate by an implanted device. The implanted device applies pacing pulses to the right atrium with a pair of small, closely spaced, electrodes, generally referred to as a bipolar electrode pair. The electrodes are carried on an implantable endocardial lead. The lead is designed for fixation in the right atrium, either by tines or by a helical screw-in tip which can serve as one of the electrodes. Both forms of fixation are well known in the art.

One potential problem with atrial antitachycardia pacing is an inadvertent dislodgment of the right atrial endocardial lead. Should the lead become dislodged, the atrial pacing electrodes could be displaced to a position close to or within the right ventricle. High rate antitachycardia pacing intended for the right atrium with the lead in such a dislodged position could cause the ventricles to be overdrive paced. This presents the possibility of accelerating the ventricles into a dangerous and potentially life threatening arrhythmia.

Atrial antitachycardia pacing can still be a very useful therapy. A significant number of atrial fibrillation patients suffer from this arrhythmia. Hence, it would be advantageous to be able to incorporate this therapy into an implantable atrial defibrillator. By virtue of the present invention, atrial antitachycardia pacing may be incorporated within implantable devices, such as an atrial defibrillator.

SUMMARY OF THE INVENTION

The invention provides a method of detecting dislodgment of a right atrial endocardial lead implanted in the right atrium of a heart wherein the lead has at least one electrode. The method includes the steps of sensing atrial and ventricular activity of the heart with one other lead including first and second electrodes, establishing a first sensing period responsive to the atrial activity sensed with the at least one other lead, and establishing a second sensing period responsive to the ventricular activity sensed with the one other lead. The method further includes the steps of sensing activity of the heart with the at least one electrode of the implanted endocardial lead during the first sensing period and the second sensing period, and comparing the heart activity sensed with the at least one electrode during the first sensing period to the heart activity sensed with the at least one electrode during the second sensing period.

The invention further provides a method for detecting dislodgment of a right atrial endocardial lead implanted within a heart right atrium wherein the lead includes an electrode. The method includes the steps of sensing atrial heart activity and ventricular heart activity of the heart with one other lead during a time period, and sensing heart activity with the endocardial lead electrode during the time period. The method further includes the steps of storing the sensed atrial heart activity the sensed ventricular heart activity, and the heart activity sensed with the endocardial lead electrode, analyzing the stored heart activity to establish a first time window from the sensed atrial heart activity and a second time window from the sensed ventricular heart activity, and comparing the heart activity sensed with the endocardial lead electrode during the first time window to the heart activity sensed with the endocardial lead electrode during the second time window.

The invention still further provides a system for detecting dislodgment of an implanted right atrial endocardial lead having at least one electrode. The system includes means including one other lead for sensing atrial and ventricular activity of the heart, means for establishing a first sensing period responsive to the atrial activity sensed with the one other lead, and means for establishing a second sensing period responsive to the ventricular activity sensed with the one other lead. The system further includes means for sensing activity of the heart with the at least one electrode of the implanted endocardial lead during the first sensing period and the second sensing period, and means for comparing the heart activity sensed with the at least one electrode during the first sensing period to the heart activity sensed with the at least one electrode during the second sensing period.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein;

DETAILED DESCRIPTION OF THE PREFERRED EMBODIMENT

Figure 1:
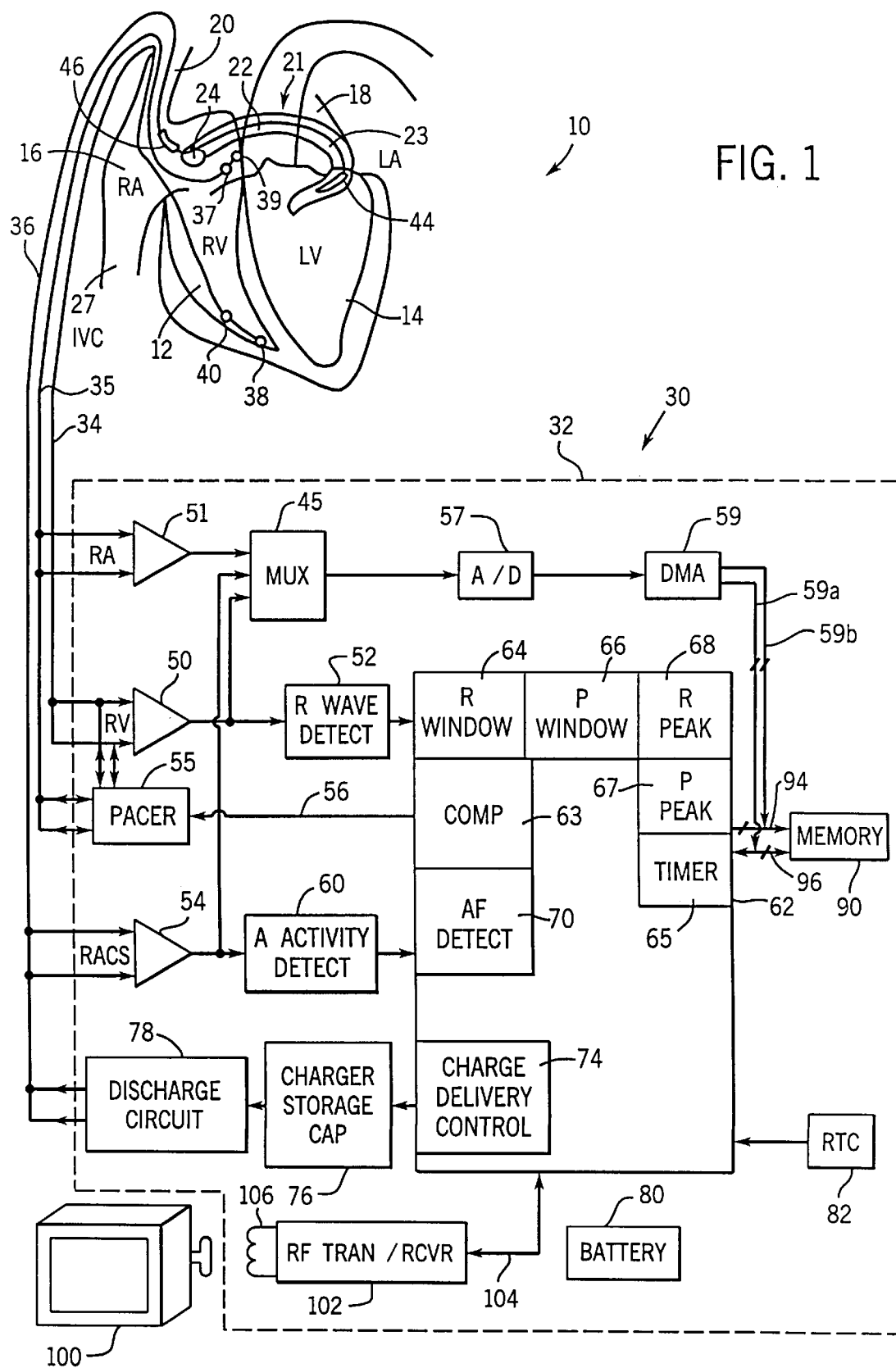
FIG. 1 is a schematic block diagram of a fully implantable atrial defibrillator embodying the present invention including a pacer and associated right atrial endocardial lead for applying atrial antitachycardia pacing to a heart.

Prior to referring to FIG. 1, a general description of a typical or normal cardiac cycle may be helpful in understanding the operation and various aspects of the present invention. The beginning of a cardiac cycle in normal sinus rhythm is initiated by a P wave which is normally a small positive wave. The P wave induces depolarization of the atria of the heart. Following the P wave there is a cardiac cycle portion which is substantially constant having a time duration on the order of, for example, 120 milliseconds.

The QRS complex of the cardiac cycle then normally occurs after the substantially constant portion. The dominating feature of the QRS complex is the R wave which is a rapid positive or negative deflection. The R wave generally has an amplitude greater than any other wave of the cardiac cycle and is characterized by a rapid deviation from and return toward baseline. The R wave is the depolarization of the ventricles. The QRS complex is completed by the S which is generally a small deflection which returns the cardiac cycle to baseline.

Following the S wave of the QRS complex, the T wave occurs which is separated from the QRS complex by about 250 milliseconds. The T wave is relatively long in duration of, for example, on the order of 150 milliseconds. The cardiac cycle segment between the S wave and the T wave is commonly referred to as the ST segment.

The next cardiac cycle begins with the next P wave. The duration of a cardiac cycle may be on the order of 800 milliseconds.

Referring now to FIG. 1, it illustrates a fully implantable atrial defibrillator 30 embodying the present invention shown in association with a schematically illustrated human heart 10. The portions of the heart 10 illustrated in the sole figure are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, and the inferior vena cava 27.

The atrial defibrillator 30 generally includes an enclosure 32 for hermetically sealing the internal circuit elements of the atrial defibrillator to be described hereinafter, a ventricular endocardial or first lead 34, a right atrial endocardial or second lead 35 and an intravascular or third lead 36. The enclosure 32 and leads 34, 35, and 36 are arranged to be implanted beneath the skin of a patient so as to render the atrial defibrillator 30 fully implantable.

The intravascular lead 36 generally includes a first or tip electrode 44 and a second proximal electrode 46. As illustrated, the lead 36 is flexible and arranged to be passed down the superior vena cava 20, into the right atrium, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18. The first electrode 44 and the second electrode 46 further provide for the delivery of defibrillating electrical energy to the atria. The electrodes 44 and 46 are preferably elongated cardioverting electrodes.

The first lead 34 preferably comprises a ventricular endocardial lead having bi-polar pair electrodes 38 and 40 arranged for establishing electrical contact with the right ventricle 12 of the heart 10. The electrodes 38 and 40 permit bi-polar sensing of ventricular activations in the right ventricle and pacing in the right ventricle. As illustrated, the lead 34 is fed through the superior vena cava 20, into the right atrium 16, and then into the right ventricle 12.

The second lead 35 preferably comprises a right atrial endocardial lead having bi-polar pair electrodes 37 and 39. Electrode 39 preferably is a helical screw-in coil for both providing fixation of the lead 35, as known in the art, and establishing electrical contact with the right atrium 16 of the heart 10. The electrodes 37 and 39 permit localized bi-polar sensing of heart activity in the right atrium and pacing, including overdrive antitachycardia pacing, in the right atrium. As illustrated, the lead 35 is fed through the superior vena cava 20 and into the right atrium 16.

Within the enclosure 32, the atrial defibrillator 30 includes a first sense amplifier 50, a second sense amplifier 51, and a third sense amplifier 54 and an R wave detector 52. The first sense amplifier 50 forms an RV channel which provides an electrogram of the sensed right ventricular heart activity at an input of multiplexer 45 and to an input of an R wave detector 52. The second sense amplifier 51 forms an RA channel to provide an electrogram of the sensed right atrial heart activity at its output which is coupled to another input of multiplexer 45. The third sense amplifier 54 forms an RACS channel to provide an electrogram of the sensed right atrium to left atrium heart activity at its output which is coupled to another input of the multiplexer 45 and an atrial activity detector 60. The sense amplifiers may include a differentiating filter so that the electrograms which they provide are differentiated electrogram signals.

The R wave detector 52 provides one or more output pulses for each R wave sensed during a cardiac cycle of the heart. To that end, the R wave detector may include a further differentiating filter for differentiating the differentiated cardiac signal provided by sense amplifier 50 resulting in a twice differentiated second cardiac signal. The R wave detector 52 may further include a threshold circuit for setting an upper and lower threshold which provides an output when the twice differentiated second cardiac signal transitions beyond either the upper or lower thresholds.

Finally, the R wave detector preferably further includes an output pulse rate limiter (not shown) having a programmable pulse repetition time interval. The pulse repetition time interval is set to be as short as possible to allow detection of the last threshold crossing for an R wave. The R wave detector 52 thus provides at least one such pulse to indicate the beginning of each detected R wave and one such pulse to indicate the completion of each detected R wave so that the beginning and end of each R wave may be determined.

The atrial activity detector 60 also preferably includes a similar further differentiating filter (not shown) and output pulse rate limiter (not shown). This similarly enables the atrial activity detector 60 to provide at least one output pulse to indicate the beginning of each sensed P-wave and another to indicate the end of each sensed P wave.

The enclosure 32 of the atrial defibrillator 30 further includes a microprocessor 62. The microprocessor 62 is preferably implemented in accordance with this embodiment of the present invention to result in a plurality of functional stages. The stages include a comparator stage 63, an R window stage 64, a timer 65, a P window stage 66, a P peak stage 67 an R peak stage 68, an atrial arrhythmia detector in the form of an atrial fibrillation detector 70 and a charge delivery and energy control stage 74.

The microprocessor 62 is arranged to operate in conjunction with a memory 90 which is coupled to the microprocessor 62 by a multiple-bit address bus 94 and a bi-directional multiple-bit data bus 96. This permits the microprocessor 62 to address desired memory locations within the memory for executing write or read operations. During a write operation, the microprocessor stores data, such as time stamps, or operating parameters, in the memory at the addresses defined by multiple-bit addresses conveyed over the address bus 94 and conveys the operating parameters and data to the memory 90 over the multiple-bit data bus 96. During a read operation, the microprocessor 62 obtains data or operating parameters from the memory at the storage locations identified by the multiple-bit addresses provided over the address bus 94 and receives the operating parameters and data from the memory over the bi-directional data bus 96.

For entering operating parameters into the memory 90, the microprocessor 62 receives the programmable operating parameters from an external controller 100 which is external to the skin of the patient. The external controller 100 is arranged to communicate with a receiver/transmitter 102 within enclosure 32 which is coupled to the microprocessor 62 over a bi-directional bus 104. The receiver/transmitter 102 conveys various information which it obtains from the microprocessor 62 to the external controller 100 or receiver programming parameters from the external controller 100 which the receiver/transmitter 102 then conveys to the microprocessor 62 for storage in memory 90.

The receiver/transmitter 102 includes a transmitting coil 106 so that the receiver/transmitter 102 and coil 106 form a communication means. Such communication means are well known in the art and may be utilized as noted above for receiving commands from the external controller 100 and for transmitting data to the external controller 100. One preferred communication system is disclosed in copending U.S. Pat. No. 5,342,408 which issued on Aug. 30, 1994 for "Telemetry System for an Implantable Cardiac Device," which patent is assigned to the assignee of the present invention and incorporated herein by reference.

The atrial defibrillator 30 further includes an analog to digital converter 57 and a direct memory access controller (DMA) 59. The analog to digital converter 57 has an input coupled to the output of the multiplexer 45 for receiving the electrogram signals generated by the sense amplifiers 50, 51, and 54. During a data acquisition, the analog to digital converter 57 converts the electrogram signals into digital data. The digital data is received by the DMA 59 and conveys the digital data to memory 90 over a data bus 59a for storage in memory at predetermined locations selected by the DMA 59 over an address bus 59b. The electrogram signals thus stored in digital form representing activity of the heart are thereafter utilized by the microprocessor to perform various functions. For example, for atrial fibrillation detection, the atrial fibrillation detector 70 utilized the store data from the RACS channel for detecting the presence of atrial fibrillation of the heart. For detecting dislodgment of the lead 35 in accordance with a preferred embodiment of the present invention, it may utilize digital electrogram data from each of the RV, RA, and RACS channels.

The atrial defibrillator 30 further includes a charger and storage capacitor circuit 76 of the type well known in the art which charges a storage capacitor to a selected peak voltage and a discharge circuit 78 for discharging the storage capacitor within circuit 76 for a predetermined time to provide a controlled discharge output of electrical energy when required to the atria of the heart. To that end, the discharge circuit 78 is coupled to the first electrode 44 and the second electrode 46 of lead 36 for applying the cardioverting or defibrillating electrical energy to the atria. The defibrillator 30 further includes a depletable power source 80, such as a lithium battery, for providing power to the electrical components of the atrial defibrillator 30, and a real time clock 82.

The atrial defibrillator 30 lastly includes a pacer 55 which is coupled to electrodes 38 and 40 of lead 34 and to electrodes 37 and 39 of lead 35. The pacer 55 preferably includes circuitry for sensing ventricular activity with electrodes 38 and 40 and pacing circuitry for applying pacing pulses to the ventricles with electrodes 38 and 40. Similarly, the pacer 55 preferably includes circuitry for sensing atrial activity with electrodes 37 and 39 and pacing circuitry for applying pacing pulses including antitachycardia atrial overdrive pacing to the atria with electrodes 37 and 39. Further, the pacer 55 may provide single chamber pacing in either the right ventricle 12 or right atrium 16, asynchronously or on demand, or dual chamber pacing. Such pacers and modalities are well known in the art. The pacer is coupled to the microprocessor over a line 56 to permit the microprocessor to configure the pacer 55 for any one of its pacing modalities including the antitachycardia atrial overdrive pacing modality.

To briefly describe the operation of the atrial defibrillator for cardioverting atrial fibrillation of the heart, an atrial fibrillation detection is initiated by the sense amplifiers 50 and 54, the R wave detector 52, the atrial activity detector 60, the analog to digital converter 57, the multiplexer 45 and the DMA 59 being enabled. A data acquisition is first performed for a data acquisition period of, for example, eight seconds. During the eight second data acquisition period, the electrogram signals from sense amplifiers 50 and 54 are digitized by the analog to digital converter 57 into digital data and the digital data is caused to be stored in the memory 90 by the DMA 59 as previously described. Also during this time, each output of the R wave detector 52 causes an interrupt to the microprocessor 62. Each R wave interrupt is time stamped and the interrupt time stamps are stored in the memory 90 along with the digital data from DMA 59.

After the eight second data acquisition period is completed, the atrial fibrillation detector 70 is enabled and analyzes the stored electrogram data from the RACS channel. The atrial fibrillation detector 70 may determine if the atria 16 and 18 are in fibrillation in a manner known in the art as, for example, described in U.S. Pat. No. 5,486,199 which issued on Jan. 13, 1996 for "System and Method For Reducing False Positives In Atrial Fibrillation Detection," which patent is assigned to the assignee of the present invention and incorporated herein by reference. If the atria are in fibrillation and thus in need of cardioversion, the charge delivery control 74 causes the charger and storage capacitor circuit 76 to charge the storage capacitor within the circuit 76 to a selected peak voltage. After the capacitor is charged, another data acquisition is performed and the atrial fibrillation detector 70 confirms the presence of atrial fibrillation. Thereafter, and in timed relation to a detected R wave, the discharge circuit 78, applies a portion of the stored electrical energy to electrodes 44 and 46 and thus the atria 16 and 18 to cardiovert the atria 16 and 18.

In accordance with a preferred embodiment of the present invention, prior to detecting if the lead 35 has become dislodged, it is preferred that a detection for atrial fibrillation be performed to make sure that the heart is in normal sinus rhythm. This may be performed as previously described by initiating a data acquisition followed by atrial fibrillation detection by the atrial fibrillation detector 70.

If the heart is in normal sinus rhythm, the lead dislodgment detection is begun by first acquiring electrograms from the RA and RACS sense channels. This is accomplished by enabling sense amplifiers 50 and 54, the multiplexer 45, the analog to digital converter 57, and the DMA 59. The electrogram data representing the RA and RACS electrograms are stored in memory 90 by the DMA 59 during the electrogram acquisition. The electrogram acquisition need only last for one complete cardiac cycle. However, additional cycles may be desirable to afford checks on electrogram signal quality, for example.

Next, from the RACS electrogram data, the R window stage 64 analyzes the data and identifies an R wave. This may be seen in FIG. 2 wherein the electrogram 200 is the RACS electrogram and the R wave 204 is identified.

Figure 2:
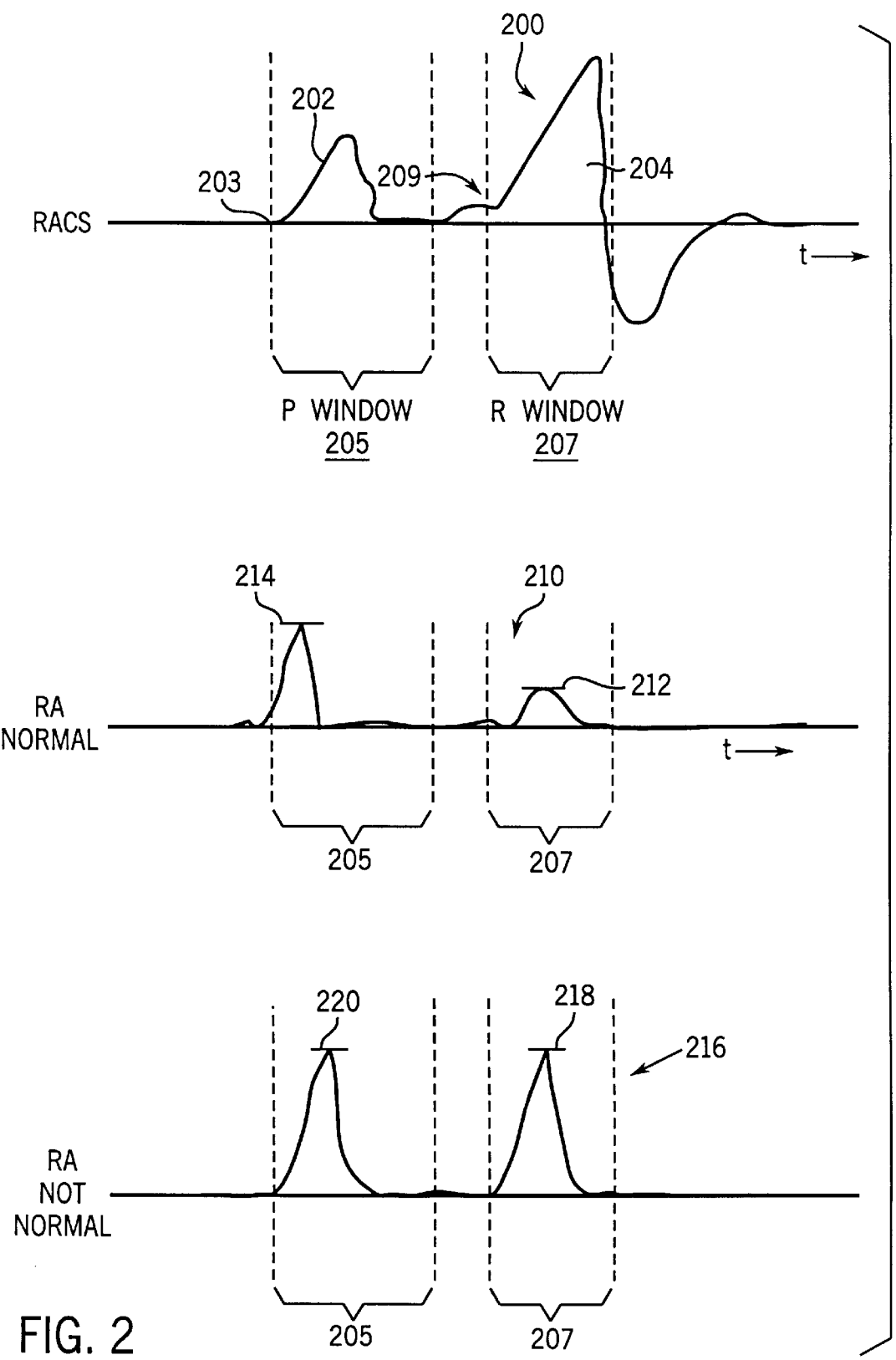
FIG. 2 is a series of electrograms illustrating the present invention in accordance with a preferred embodiment thereof.

Next, the P window stage 66 identifies a P wave in the RACS electrogram from the RACS electrogram data. Again, the RACS electrogram is shown in FIG. 2 as electrogram 200. The P wave 202 and R wave 204 may be readily distinguished from each other by virtue of their time displacement and serial activation sequential order.

Either from the analysis of the electrogram 200 or from time stamped interrupts generated by the R wave detector 52 and atrial activity detector 60, the first detected P wave event and first detected R wave event are denoted as P start 203 and R start 209 respectively by the P window stage 64 and R window stage 66 respectively. These stages then define respective sensing periods or windows. The P window stage 64 defines a first sensing period or P window 205 which begins on P start and ends before R start, for example, 40 milliseconds before R start. The R window stage 66 defines a second sensing period or R window 207 which begins on R start and ends a fixed time thereafter, for example, 100 milliseconds after R start to assure completion of the R wave 208.

Once the P window 205 and R window 207 are defined, the RA electrogram, obtained from electrodes 37 and 39 of lead 35, is analyzed during the P window 205 and R window 207. More specifically, the RA electrogram portion during the P window 205 is compared to the RA electrogram portion during the R window 207. In accordance with this preferred embodiment, the absolute peak values of the RA electrogram during these time periods are compared to determine if lead 35 has been dislodged with electrodes 37 and 39 migrating near to or within the right ventricle 12. The absolute peak value of the RA electrogram during the P window 205 (P peak) is determined by the P peak stage 67. The absolute peak value of the RA electrogram during the R window 207 (R peak) is determined by the R peak stage 68. The peak values are then compared by the comparator stage 63. If the comparison satisfies a predetermined criteria, the lead is considered to be dislodged and overdrive atrial antitachycardia pacing is disabled. For example, if R peak is larger than a certain percentage, say 75%, of P peak, then lead 35 may be considered to be dislodged.

The above criteria accurately detects the dislodgment of lead 35. Since electrodes 37 and 39 are a bi-polar electrode pair nominally within the right atrium, the RA electrogram generated by these electrodes should have a relatively small peak amplitude during the R window as compared to its peak amplitude during the P window. The Electrogram 210 of FIG. 2 illustrates an exemplary RA electrogram for a non-dislodged lead 35. Here it can be seen that the R peak 212 is much less than 75% of P peak 214. However, electrogram 216 of FIG. 2 illustrates an exemplary RA electrogram for a dislodged lead 35. Here, R peak 218 is much larger than 75% of P peak 220. Of course, other features of the RA electrogram during the P window and R window or peak comparative factors may be used for comparison in accordance with the broader aspects of the present invention as would be appreciated by those skilled in the art.

The detection for lead dislodgment may be performed at spaced apart times such as periodically. This may be accomplished by the timer 65 activating the detection sequence once each day, for example. Alternatively, the timer 65 may be used to periodically initiate an atrial fibrillation detection for rhythm classification followed by a lead dislodgment detection in accordance with the present invention.

While particular embodiments of the present invention have been shown and described, modifications may be made, and it is therefore intended in the appended claims to cover all such changes and modifications which fall within the true spirit and scope of the invention.

What is claimed is:

1. A method of detecting dislodgment of a right atrial endocardial lead implanted in the right atrium of a heart, the lead having at least one electrode, said method including the steps of:

sensing atrial and ventricular activity of the heart with one other lead including first and second electrodes;

establishing a first sensing period responsive to the atrial activity sensed with the one other lead;

establishing a second sensing period responsive to the ventricular activity sensed with the one other lead;

sensing activity of the heart with the at least one electrode of the implanted endocardial lead during the first sensing period and the second sensing period; and comparing the heart activity sensed with the at least one electrode during the first sensing period to the heart activity sensed with the at least one electrode during the second sensing period.

2. A method as defined in claim 1 including the further step of implanting the first electrode within the right atrium of the heart and implanting the second electrode within the coronary sinus of the heart.

3. A method as defined in claim 1 wherein the first recited establishing step includes isolating a P wave from the sensed atrial activity and commencing the first sensing period with the beginning of the isolated P wave.

4. A method as defined in claim 3 wherein the first recited establishing step includes terminating the first sensing period before the occurrence of a next succeeding R wave of the heart.

5. A method as defined in claim 1 wherein the first recited establishing step includes isolating an R wave from the sensed ventricular activity and commencing the second sensing period with the beginning of the isolated R wave.

6. A method as defined in claim 5 wherein the second recited establishing step includes terminating the second sensing period after the isolated R wave.

7. A method as defined in claim 6 wherein the second recited establishing step includes terminating the second sensing period a predetermined time after the commencement of the second sensing period.

8. A method as defined in claim 1 further including determining a first peak amplitude of the heart activity sensed during the first sensing period and a second peak amplitude of the heart activity sensed during the second sensing period, and wherein the comparing step includes comparing the second peak amplitude to the first peak amplitude.

9. A method as defined in claim 1 including an initial step of determining that the heart is in normal sinus rhythm.

10. A method as defined in claim 9 including repeating the recited steps at spaced apart times.

11. A method as defined in claim 9 including repeating the recited steps once each day.

12. A method of detecting dislodgment of a right atrial endocardial lead implanted within a heart right atrium, the lead including an electrode, the method including the steps of:

sensing atrial heart activity and ventricular heart activity of the heart with one other lead during a time period;

sensing heart activity with the endocardial lead electrode during the time period;

storing the sensed atrial heart activity, the sensed ventricular heart activity, and the heart activity sensed with the endocardial lead electrode;

analyzing the stored heart activity to establish a first time window from the sensed atrial heart activity and a second time window from the sensed ventricular heart activity; and comparing the heart activity sensed with the endocardial lead electrode during the first time window to the heart activity sensed with the endocardial lead electrode during the second time window.

13. A system for detecting dislodgment of an implanted right atrial endocardial lead having at least one electrode, the system comprising:

means including one other lead for sensing atrial and ventricular activity of the heart;

means for establishing a first sensing period responsive to the atrial activity sensed with the one other lead;

means for establishing a second sensing period responsive to the ventricular activity sensed with the one other lead;

means for sensing activity of the heart with the at least one electrode of the implanted endocardial lead during the first sensing period and the second sensing period; and means for comparing the heart activity sensed with the at least one electrode during the first sensing period to the heart activity sensed with the at least one electrode during the second sensing period.

* * * * *